(12) United States Patent
Chinnayelka et al.

(10) Patent No.: US 9,547,005 B2
(45) Date of Patent: *Jan. 17, 2017

(54) TEST STRIP WITH MAGNETO-ELASTIC-RESONANCE SENSOR

(71) Applicant: Ascensia Diabetes Care Holdings AG, Basel (CH)

(72) Inventors: Swetha Chinnayelka, Derry, NH (US); Jiangfeng Fei, New Providence, NJ (US); Yuan Wang, Mountain Lakes, NJ (US); Narasinha Parasnis, Nanuet, NY (US); Hoi-Cheong Steve Sun, Lexington, MA (US); Raeann Gifford, Burbank, CA (US); Steven C. Charlton, Osceola, IN (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 278 days.

This patent is subject to a terminal disclaimer.

(21) Appl. No.: 14/255,526

(22) Filed: Apr. 17, 2014

(65) Prior Publication Data

US 2014/0227771 A1     Aug. 14, 2014

Related U.S. Application Data

(63) Continuation of application No. 13/163,043, filed on Jun. 17, 2011, now Pat. No. 8,702,967.

(Continued)

(51) Int. Cl.
```
G01N 33/543    (2006.01)
G01N 33/66     (2006.01)
G01N 33/80     (2006.01)
```

(52) U.S. Cl.
CPC ........ *G01N 33/54373* (2013.01); *G01N 33/66* (2013.01); *G01N 33/80* (2013.01); *Y10T 436/144444* (2015.01)

(58) Field of Classification Search
CPC ............... C12Q 1/00; C12Q 1/02; C12Q 1/34; C12Q 1/54; G01N 27/327; G01N 27/3272; G01N 27/48; G01N 27/26; G01N 33/487; A61B 5/05; A61B 5/14532

See application file for complete search history.

(56) References Cited

U.S. PATENT DOCUMENTS 4,721,677 A    1/1988  Clark, Jr.
6,397,661 B1   6/2002  Grimes et al.
(Continued)

FOREIGN PATENT DOCUMENTS

WO        2004021944 A1    3/2004
WO    WO 2004/021944        3/2004
(Continued)

OTHER PUBLICATIONS

Cai et al., "A wireless, remote queryglucose biosensor based on a pH-sensitive polymer", Analytical Chemistry 2004, vol. 76, No. 14, 4038-4043, Jul. 15, 2004.

(Continued)

*Primary Examiner* — Luan Van
*Assistant Examiner* — Maris R Kessel
(74) *Attorney, Agent, or Firm* — Dugan & Dugan, PC

(57) ABSTRACT

A test meter system for testing a characteristic of a fluid, the test meter system including a test meter having a housing with an opening adapted to accept a test strip, an interrogation coil within the housing, a pick-up coil within the housing, and a test strip including at least one magneto-elastic-resonance sensor. When the test strip is within the opening, the interrogation coil may utilize magneto-elastic-resonance technology to interrogate the magneto-elastic-resonance sensor and the pick-up coil may be used to sense a resultant oscillation frequency of the magneto-elastic- (Continued)

resonance sensor, the resultant oscillation frequency associated with the characteristic. The test strip may include a plurality of sensors. The sensors may be coated with a coating sensitive to a characteristic of the fluid, where the interrogation reveals information about the fluid characteristic.

20 Claims, 4 Drawing Sheets

Related U.S. Application Data

(60) Provisional application No. 61/355,731, filed on Jun. 17, 2010.

(56) References Cited

U.S. PATENT DOCUMENTS

| | | | |
|---|---|---|---|
| 6,688,162 | B2 | 2/2004 | Bachas et al. |
| 7,176,344 | B2 | 2/2007 | Gustafson et al. |
| 7,364,699 | B2 | 4/2008 | Charlton |
| 7,549,323 | B2 | 6/2009 | Charlton et al. |
| 7,749,454 | B2 | 7/2010 | Charlton |
| 8,702,967 | B2 | 4/2014 | Chinnayelka et al. |
| 2003/0047451 | A1 | 3/2003 | Bhullar et al. |
| 2006/0127964 | A1 | 6/2006 | Ford et al. |
| 2006/0182656 | A1 | 8/2006 | Funke et al. |
| 2007/0259431 | A1 | 11/2007 | Charlton |
| 2008/0261261 | A1 | 10/2008 | Grimes et al. |
| 2009/0151448 | A1 | 6/2009 | Nishina |
| 2010/0036407 | A1 | 2/2010 | Fowler |
| 2010/0241030 | A1 | 9/2010 | Fowler et al. |
| 2010/0319436 | A1 | 12/2010 | Sun et al. |
| 2012/0073968 | A1 | 3/2012 | Lee et al. |
| 2013/0048495 | A1 | 2/2013 | Charlton |

FOREIGN PATENT DOCUMENTS

| | | |
|---|---|---|
| WO | 2007073258 A1 | 6/2007 |
| WO | WO 2007/073258 | 6/2007 |
| WO | 2007142561 A1 | 12/2007 |
| WO | WO 2007/142561 | 12/2007 |
| WO | 2008076005 A1 | 6/2008 |
| WO | WO 2008/076005 | 6/2008 |
| WO | WO 2011/002152 | 1/2011 |

OTHER PUBLICATIONS

Cai et al., "A wireless, rmote query manetoelastic CO2 sensor", J. Environ. Monit., 2000, 2, 556-560.
Grimes et al. (Biomedical Microdevices 2:1, 51-60, 1999).
Grimes et al., "Wireless magnetoelastic resonance sensors: A critical review", Sensors 2002, 2, 294-313.
Grimes, et al. (Journal of Applied Physics, 2000).
Puckett, et al. (Biosensors and Bioelectronics, 18, 2003, 675-681).
Stoyanov et al., "A remote query magnetostrictive viscosity sensor", Sensors and Actuators 80 (2000) 8-14.
International Search Report and Written Opinion of International Application No. PCT/US2012/051539 (BHDD/028/US) dated Nov. 6, 2012.
International Preliminary Report on Patentability and Written Opinion of International Application No. PCT/US2012/051539 (BHDD/028/WO) dated Mar. 6, 2014.
Charlton, U.S. Appl. No. 14/935,256 (BHDD/028/US/D01), titled: "Analyte Sensors and Systems Including Retention Tab and Methods of Manufacturing Same," filed Nov. 6, 2015.
Grimes et al., "Thin-Film Magnetoelastic Microsensors for Remote Query Biomedical Monitoring," Biomedical Microdevices 2:1, 51-60, 1999.
Puckeet et al., "Monitoring blood coagulation with magnetoelastic sensors," Biosensors and Bioelectronics, 18, 2003, 675-681.
Grimes et al., "Magnetoelastic sensors in combination with nanometer-scale honeycombed thin film ceramic TiO2 for remote query measurement of humidity," Journal of Applied Physics, vol. 87, No. 9, 2000.

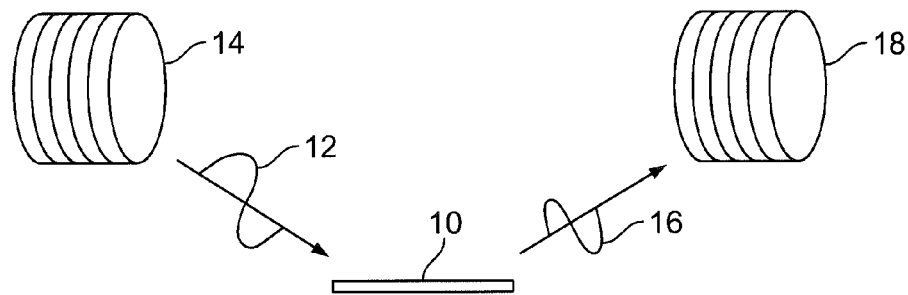
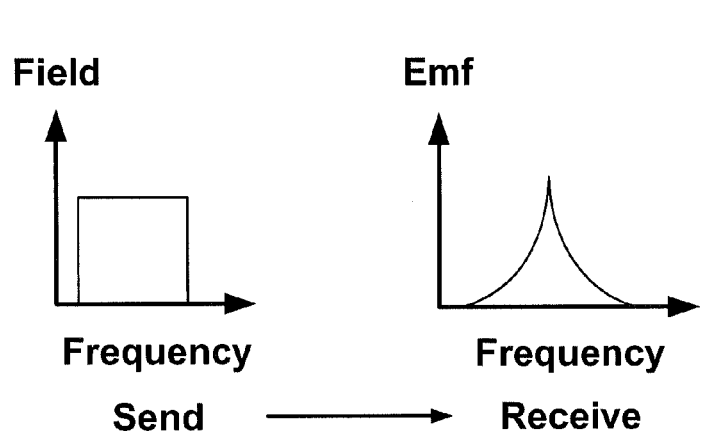
FIG. 1A
(PRIOR ART)
FIG. 1B
(PRIOR ART)
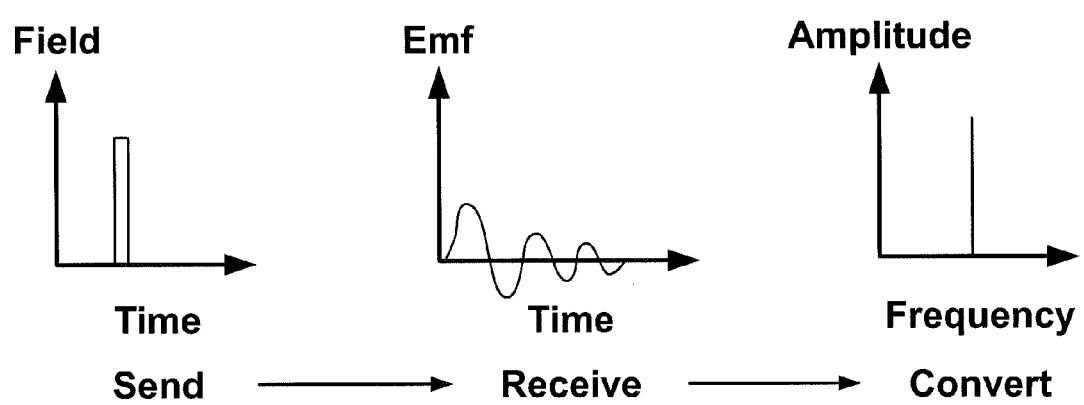
FIG. 1C
(PRIOR ART)

TEST STRIP WITH MAGNETO-ELASTIC-RESONANCE SENSOR

CROSS-REFERENCE TO RELATED APPLICATIONS

The present application is a continuation of U.S. patent application Ser. No. 13/163,043, filed Jun. 17, 2011, and claims the benefit of the filing date of U.S. Provisional Patent Application No. 61/355,731 filed Jun. 17, 2010, the disclosures of which are hereby incorporated herein by reference.

BACKGROUND OF THE INVENTION

Immunoassay test strips are well known devices for measuring concentrations of substances found in biological liquids. Typically, a user will deposit a test sample of the biological liquid on a sample receiving pad either in fluid communication with the test strip, or forming a portion of the test strip. The biological liquid sample is permitted to wick along the test strip to a predefined testing area that includes a reagent capable of a readable change when contacted by a predetermined constituent in the test sample, such as by changing color.

For purposes of this disclosure, test strips will be described in relation to glucose (HbA1c) testing for those afflicted with diabetes. However, test strips are also commonly used for many other purposes, such as drug use testing, pregnancy (hCG level) testing, or pH testing.

For HbA1c testing, a user deposits a sample of blood, which may be diluted, on the sample receiving pad associated with the test strip. The blood then wicks along the test strip to the reagent area where a color change may occur. The degree of the color change or the color itself is correlated to a concentration of HbA1c in the test sample. Similarly, the absence of a color change indicates that the level of HbA1c is below that which is detectable by the particular strip.

Some test strips can be read by a human eye while others require sophisticated equipment, such as a spectrophotometer capable of reading reflectance values. It is necessary that such spectrophotometers be as accurate as possible. For those with diabetes, entire treatment protocols may be established or adjusted based on the level of HbA1c found in the blood at a particular time.

Many factors affect the accuracy of test strips. In the glucose testing area, it is well known that temperature and viscosity play important roles. Test meters may therefore be calibrated, which is often referred to as "compensated," for these factors. Existing methods of compensating are known.

SUMMARY OF THE INVENTION

Better methods of compensation, and methods for "total compensation," where multiple tests and adjustments are made simultaneously, would be advantageous. In addition, "total compensation" using a single calibration method would also be advantageous. In order to achieve these better methods, the use of specialized magneto-elastic-resonance sensors within test strips is contemplated.

It would also be advantageous to use specialized magneto-elastic-resonance sensors to test for factors previously not capable of being tested for. For example, an actual temperature reading at the reagent site cannot presently be tested for absent magneto-elastic-resonance technology.

Lastly, it would also be advantages to use magneto-elastic-resonance sensors for autocoding purposes, to prevent non-authorized test strips from being used with certain meters.

The magneto-elastic-resonance may also advantageously utilized to prevent wasteful use of sensor strips as well as to initiate testing.

Magneto-elastic-resonance sensors may be used within test strips in accordance with certain aspects of the present invention. In accordance with one aspect, there is provided a glucose test meter incorporating magneto-elastic-resonance technology for interrogating characteristics of a glucose test strip in the reagent area, along with a glucose test strip incorporating at least one magneto-elastic-resonance sensor in the reagent area. The magneto-elastic-resonance sensor may be coated with a coating that is responsive to the characteristic being tested for. Among these characteristics are fill level, humidity, glucose level, temperature, viscosity/hematocrit level, as well as others.

In accordance with further aspects of the present invention, a single magneto-elastic-resonance sensor may be capable of being interrogated for at least two characteristics. Such characteristics may be any combination of quantitative and non-quantitative tests. If quantitative, the test meter may include deconvolution algorithms to extract the particular characteristics from a single measurement. An example of this aspect of the invention is a single sensor capable of testing for humidity and temperature.

In a still further aspect of the invention, the temperature of a reaction on a test strip may be measured directly at the reaction site using a sensor with magneto-elastic-resonance technology. A second sensor may be located at a separate area of the test strip to aid with calibration. A still further sensor may be located on or in the test meter to further aid calibration.

In an additional aspect of the present invention, "total compensation" of a test strip may be achieved solely through the use of magneto-elastic-resonance technology. Such "total compensation" may entail interrogation and calibration for humidity, temperature of the reaction, glucose level, hematocrit level, and viscosity, among other characteristics.

In further aspects of the invention, magneto-elastic-resonance technology may be used to autocode test strips for security or other purposes.

In accordance with other aspects of the invention, a test meter system for testing a characteristic of a fluid comprises a test meter having a housing with an opening adapted to accept a test strip, an interrogation coil within the housing, a pick-up coil within the housing, and a test strip including at least one magneto-elastic-resonance sensor. When the test strip is within the opening, the interrogation coil may utilize magneto-elasticresonance technology to interrogate the magneto-elastic-resonance sensor and the pick-up coil senses a resultant oscillation frequency of the magneto-elastic-resonance sensor, the resultant oscillation frequency associated with the characteristic.

The pick-up coil may sense the resultant oscillation frequency as the interrogation coil interrogates the sensor.

The test strip may contain a cavity. The sensor may be within the cavity. A second sensor may be outside of the cavity. The sensor may be nearer a top portion of the cavity than a bottom portion.

The sensor may be coated with a characteristic sensitive coating.

The test meter system may further comprising a second sensor, the sensor and second sensor both being located adjacent a cavity of the test strip, wherein the sensor may be coated with a humidity sensitive coating and the second sensor may be coated with a temperature sensitive coating.

The sensor may be coated with a coating sensitive to at least one of temperature, viscosity, glucose, and humidity.

The test meter system may further comprise a second sensor, wherein the first sensor is located in a flow path of sample fluid applied to the test strip before the second sensor, the test strip further comprising a cavity between the sensor and the second sensor. The meter may initiate a power-up procedure when the sensor is wetted with sample fluid and the meter may begin a testing procedure when the second sensor is wetted with sample fluid. The system may further comprise a third sensor coated with a temperature sensitive coating and a fourth sensor coated with a humidity sensitive coating. The third sensor and the fourth sensor may be located directly adjacent to the cavity.

In a further aspect, a test strip for testing a characteristic of a fluid may comprise a body of wicking material and a a magneto-elastic-resonance sensor.

The test strip may further comprise a cavity. The sensor may be within the cavity.

The test strip may further comprise a plurality of sensors.

In a still further aspect, a test meter for testing a characteristic of a fluid, the test meter comprises a housing with an opening adapted to accept a test strip, an interrogation coil within the housing, and a pick-up coil within the housing. When a test strip having a magneto-elastic-resonance sensor is within the opening, the interrogation coil may utilize magneto-elastic-resonance technology to interrogate the magneto-elastic-resonance sensor and the pick-up coil may sense a resultant oscillation frequency of the magneto-elastic-resonance sensor, the resultant oscillation frequency associated with the characteristic.

In a still further aspect, a method of interrogating a test strip to identify a characteristic of a fluid sample comprises applying a fluid sample to a test strip, wherein the fluid sample wets a magneto-elastic-resonance sensor associated with the test strip, interrogating the sensor with a magneto-elastic-resonance interrogation coil, reading a resultant oscillation frequency of the sensor with a pick-up coil, and identifying a characteristic of the fluid sample based on the resultant oscillation frequency.

BRIEF DESCRIPTION OF THE DRAWINGS

Other advantages and features of the invention are described with reference to exemplary embodiments, which are intended to explain and not to limit the invention, and are illustrated in the drawings in which:

FIGS. 1a-1c depict different examples of magneto-elastic-resonance technologies;

DETAILED DESCRIPTION

Figure 2A:
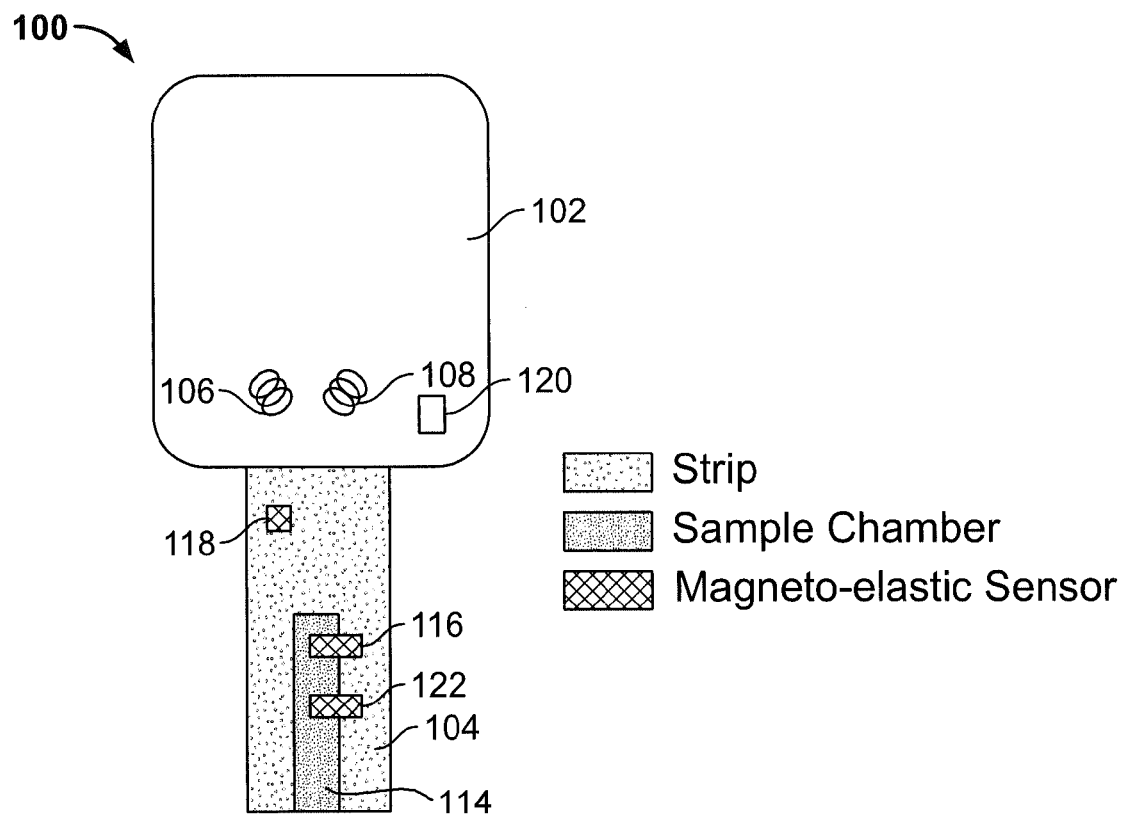
FIGS. 2a-2d depict arrangements of magneto-elastic-resonance technology in a blood glucose meter system in accordance with embodiments of the present invention.

The following discussion describes, in detail, various aspects and embodiments of the present invention. This discussion should not be construed as limiting the invention to those particular aspects or embodiments. Rather, practitioners skilled in the art will recognize numerous other aspects and embodiments as well, which are within the scope of the present invention.

In describing the preferred embodiments of the present invention illustrated in the drawings, specific terminology will be used for the sake of clarity. However, the present invention is not intended to be limited to the specific terms so selected, and it is to be understood that each specific term includes all technical equivalents that operate in a similar manner to accomplish a similar purpose.

For purposes of explanation, the invention is generally described herein with regard to glucose test meters and test strips. However, it is to be understood that the compensation methods discussed herein may be used for other applications involving testing where compensation may be advantageous.

It is preferable to provide compensation where the compensating tests are consistent, and adjustments may be made promptly. The present invention contemplates a test protocol involving magneto-elastic-resonance sensors to achieve this result.

The use of magneto-elastic-resonance sensor technology involves placing an alloy (or non-alloy) acting as a sensor in an area of interest and reading oscillations from the alloy after excitation of the alloy. Typically, the alloy will be a very thin strip of material, as known in the magneto-elastic-resonance arts. As shown in FIG. 1a, a generic view of magneto-elastic-resonance operation, the alloy 10 is excited remotely by applying a magnetic field 12 from an interrogation coil 14, also referred to as a drive coil. The excited alloy 10 oscillates due to magneto-elastic effects. This oscillation emits a resultant magnetic flux 16 with a particular characteristic resonance frequency, which may be picked-up or otherwise read remotely by a pick-up coil 18. The alloy 10 may be coated with a coating to aid in the determination of the parameter or characteristic that the alloy sensor will test for. In this regard, the alloy 10 may be coated with a coating that is sensitive to the factor for which testing is desired. For example, in testing for humidity, the alloy 10 may be coated with a humidity sensitive coating that swells in circumstances of increased humidity. Such swelling alters the characteristic resonance frequency of the new alloy by an amount that may be calibrated in test procedures, leading to measureable results following later interrogation. For example, a first humidity level may lead to a characteristic resonance frequency of one recordable and repeatable value while a second humidity level may lead to another recordable and repeatable value. Thus, when the humidity level is unknown, it may be determined by calibrated magneto-elastic-resonance techniques.

Generally, there are two methods of remotely interrogating magneto-elastic-resonance sensors, continuously or as a pulse measurement.

Continuous measurements mean that the magneto-elastic-resonance sensor is simultaneously excited and detected during the measurement. The frequency of the exciting field is varied during the measurement and the frequency response of the sensor is recorded. The main challenge in this type of system is to separate the relatively strong excitation field from the relatively weak sensor response. The relative frequency strengths and durations for a continuous system are shown in FIG. 1b.

Pulsed measurements are obtained by exciting the magneto-elastic-resonance sensor in short sinusoidal magnetic pulses. Again, under these conditions, the sensor oscillates due to magneto-elastic effect. The excitation pulse is then rapidly diminished. In the meantime, the sensor continues to oscillate for a short time, often referred to as a ring-down time. During the ring-down time, the pick-up coil measures the magnetic signal emitted by the sensor. This signal is then converted to an amplitude at a given frequency using known means. Visual indication of this procedure is shown in FIG. 1c.

In comparison to the pulsed measurement method, the continuous method has a shorter sensor to reader range (typically a few centimeters), is slower (typically 5-50 seconds), and may encounter issues with crosstalk between coils. The pulsed method also has a larger sensor to reader range (typically in the 10-100 cm range), is faster (typically in the millisecond range), and has fewer issues with crosstalk. Either technique may be used with the present invention.

Where more than one sensor is associated with the test strip, the sensors may have dedicated interrogation and pick-up coils or a single pair of coils may be utilized to interrogate and pick-up each of the sensors.

In lieu of reading resonance frequency, a Q-value may be obtained from the oscillating sensor. The Q-value is obtained by taking the ratio of the resonance frequency ($f_r$) to a gamma factor ($\gamma$), where the gamma factor ($\gamma$) is the width of the resonance peak ($Q=f_r/\gamma$).

Figure 2B:
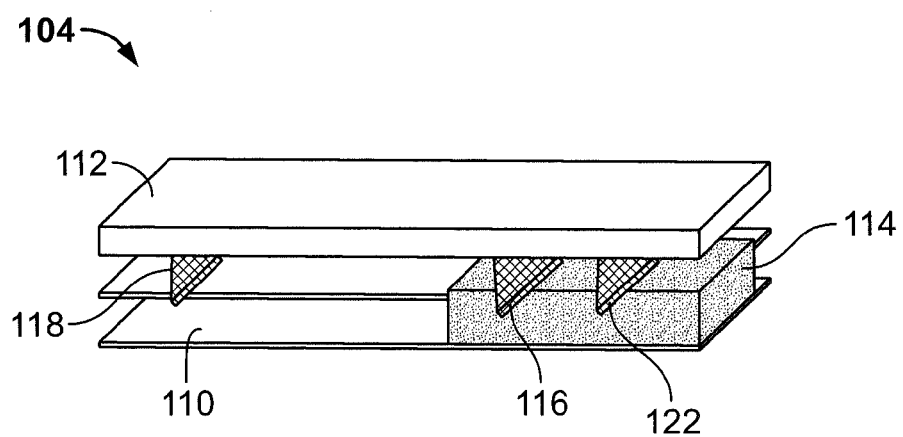

FIGS. 2a and 2b depict an arrangement of magneto-elastic-resonance technology for a glucose meter test strip in accordance with an embodiment of the invention. As shown in FIG. 2a, the system 100 may include a glucose meter 102 and a test strip 104. As with conventional test strips, test strip 104 may be inserted into the glucose meter 102 to obtain a glucose reading. This condition is shown in FIG. 2a. FIG. 2a also indicates that the test strip is provided with a sensor 116 while the glucose meter 102 is equipped with a drive coil 106 and a pickup coil 108. As discussed previously, the drive coil 106 emits a magnetic field to excite the sensor 116, whose oscillating frequency emits a second magnetic field measured by the pickup coil 102.

The test strip 104 of FIG. 2a is shown more clearly in FIG. 2b. As shown, the test strip 104 may comprise a strip 110 with a lid 112 arranged to form a cavity 114. Typically, the strip 110 is made from cellulose or other wicking material, and the lid 112 is constructed from a plastic film or other liquid impervious protective material. In this regard, the test strip 104 is not unlike conventional test strips. However, the test strip 104 of the present invention is also inclusive of a sensor 116, here placed within the cavity 114. As shown in the embodiment of FIGS. 2a,2b, the sensor 116 may be positioned within the cavity such that a portion of the strip 104 is partially positioned within the cavity and another portion of the test strip 104 is partially positioned outside of the cavity 114. The portion of the strip 110 partially positioned outside of the cavity 114 can overlap with the wicking material that is adjacent the cavity 114. As sample liquid enters the test strip from the right-hand side in the view of FIG. 2b, the sample liquid will contact the sensor 116 within the cavity 114. Typically, the test strip 104 will have been inserted into the meter 102 before this occurs. The sensor may then be interrogated by the drive coil 106 for the parameter to be tested, allowing the pickup coil 108 to obtain a response which may be evaluated and compensated for by the meter according to a predetermined calibration protocol.

Although this disclosure has discussed the presence of a single sensor within a test strip, it will be appreciated that virtually any number of sensors may be used in a test strip, with limits being physical parameters of available space and proximity. In certain applications, which will be discussed below, it is advantageous or even mandatory to include more than one sensor in a test strip. Furthermore, a single sensor may be configured to test for more than one parameter. Examples of such sensors will also be discussed below.

Among the parameters that may be tested by magneto-elastic-resonance technology in glucose test strips are glucose level, humidity, underfill, temperature, hematocrit level, viscosity level, and others.

Underfill detection for glucose and other sensor strips is important because it allows the meter to determine whether the strip has been properly filled with test fluid. More specifically, it allows the meter to determine whether the test strip has been underfilled. When the sensor is dry, a particular reading will be obtained upon sampling (sampling being magneto-elastic-resonance interrogation and reception of the output). Once the sensor is saturated with liquid, a large discrepancy is measured as compared to a dry sensor given the same interrogation parameters. This non-quantitative analysis indicates that the test strip is saturated. An example of this testing is provided below as Example 1. This technology could prevent users from wasting strips due to insufficient fluid sample level in the cavity. For example, the meter may be equipped with electronic controls to initiate operation only after the test strip is sufficiently saturated, as determined by the magneto-elastic-resonance testing. Without an indication of a sufficient level, additional sample can be applied to the strip by the user and the strip's use may continue.

Because the underfill test is non-qualitative, the sensor need not be coated with a humidity sensitive coating. Rather, the sensor may be uncoated or provided with other coatings, such as simple protective coatings. The sensor may also be coated with a coating targeted at another parameter, such as a temperature sensitive coating, to aid in the measuring of temperature at the reaction site. It has been found that such coatings will not interfere with the underfill reading.

In order to ensure that the entire test strip 110 is saturated, it is preferred that the underfill sensor 116 be placed at a relatively high level within the cavity 114. That is, the sensor 116 is preferably placed toward the top of the cavity 114 near the lid 112 and away from the bottom so a sufficiently large portion of the cavity is filled with test sample prior to the sensor being wetted. This arrangement is shown in FIG. 3, a partially exploded cross sectional view of a representative test strip.

Figure 3:
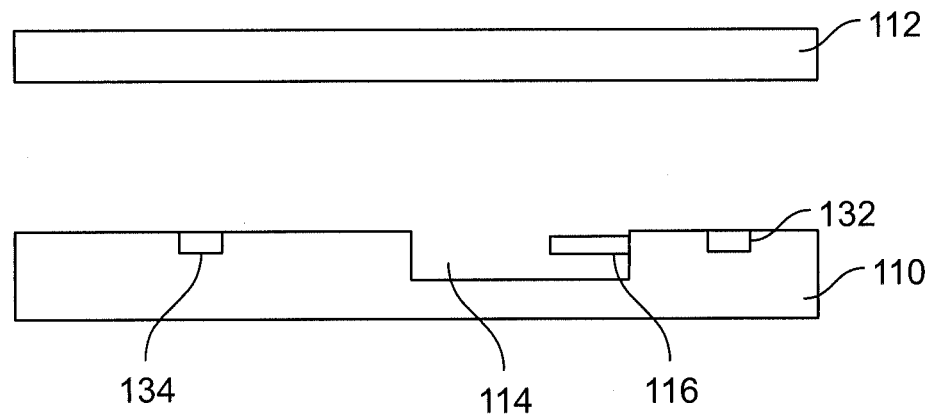
FIG. 3 depicts a partially exploded cross sectional view of a representative test strip.

Also shown in FIG. 3 are sensors 132, 134. In conventional meter systems, electrodes may be placed in test strips to initiate the testing process. Typically two electrodes are placed on the strip, with one on each side of the cavity. When a first electrode is wetted, the meter turns on. Fluid sample then flows into the cavity. When the cavity is filled, fluid sample flows past the cavity to the second electrode. When this electrode is wetted, the meter begins taking a reading. In embodiments of the present invention, the two electrodes may be replaced with magneto-electonic-resonance sensors 132, 134. Such sensors operate on similar principles, such that when sensor 132 is wetted the resonance frequency will change and the meter fully powers on—it will have previously been powered to a sufficient level to take the initial reading. Fluid sample then flows into the cavity 114. Once the cavity is filled, fluid sample flows through the test strip 110 and onto sensor 134. Once sensor 134 is wetted, the meter fully powers on begins the testing process.

Another factor that may be tested for is temperature. In conventional test strip temperature sensing techniques, the exact temperature at a reaction site of a test strip is not measured directly, but is approximated from one or more other temperature values. Using magneto-elastic-resonance technology, the temperature at the exact reaction point can be measured directly, which represents a large improvement over the art. This capability is due to the sensor's ability to be placed directly in or directly adjacent to the reaction site. When coated with a temperature sensitive coating, the sensor may be interrogated and the reactive magnetic flux measured, revealing a temperature when compared to a known calibration standard.

Humidity may also be tested for. Like the temperature test, a sensor coated with a humidity sensitive coating may be placed on various locations on the strip and interrogated. Preferably, the humidity sensor is on a surface of the strip where it can be used to measure ambient humidity in the general test area.

An understanding of the underfill test and the temperature test reveals that both tests may be conducted with a single sensor. For example, a sensor coated with a temperature sensitive coating may be interrogated when dry, revealing a particular response. When filled with sample, the sensor may again be interrogated. As described with respect to the interrogation process of underfill testing, the response obtained when saturated will represent a large differential from the dry response. This identifies that the sensor is indeed saturated. Once this saturated response is obtained, it may then be compared to calibrated temperature responses, to obtain a temperature at the reaction site.

In order to even further evaluate temperature at the reaction site, multiple sensors may be utilized to adjust the actual reading at the reaction site. In one example, a first sensor which is coated with a temperature sensitive coating may be placed on the surface of a strip near the meter. An example of such a sensor is shown in FIG. 2b as sensor 118. This sensor 118 may then be interrogated for temperature, revealing a surface temperature of the strip. A second sensor, also coated with a temperature sensitive coating, may be placed within the cavity of the test strip, for example sensor 116 of FIG. 2b, or directly adjacent to the cavity such that the temperature recorded is essentially the temperature of the reaction. This sensor 116 may also be interrogated, revealing a reading indicative of a temperature in the cavity of the test strip where a test reaction occurs (this sensor 116 may also be utilized to measure underfill if it is placed within the cavity at a level below the fill level). A thermistor or other sensor in the meter 120 may also obtain a third temperature reading ($T_m$).

Typically, once the test strip is equilibrated to the atmosphere, the temperature of the first sensor, at the test strip's surface, will not change greatly. However, it may be influenced by the meter temperature, which can vary as the meter electronics are energized thus providing heat. In the meantime, the second sensor at the cavity of the test strip will begin at ambient temperature but will move toward the temperature of the liquid sample once filled. The interrogated frequency difference between the two sensors on the strip 116, 118 is measured. From the difference between the two frequencies, a temperature differential ($\Delta T$) is established. Then the calibrated cavity temperature is quantified by subtracting the temperature difference from the meter temperature using the formula:

$$T_m - \Delta T = \text{reaction temperature.}$$

In situations where the meter temperature affects the test strip, this procedure may be a more accurate indication of the actual reaction temperature than other tests.

Another parameter that may be tested for using magneto-elastic-resonance technology is hematocrit level. To test for hematocrit level, a sensor may be coated with a hematocrit sensitive coating, that swells to varying detectable degrees under different hematocrit levels, thus altering its vibration characteristics. The sensor may then be placed on the strip in an area that will be saturated with sample fluid, such as the chamber, and interrogated.

Because hematocrit readings using such technology are related to viscosity of the fluid by known mathematical formulas, a separate viscosity sensor may not be required. However, a second sensor to provide an independent reading for viscosity may also be provided. In this manner, the second sensor may be placed within the same fluid as the sensor testing hematocrit. Such a sensor 122 is shown in FIG. 2b. This second well sensor 122 may be coated with a viscosity sensitive coating and may be interrogated for viscosity level measurement. Once the hematocrit level from the first sensor 116 and the viscosity level from the second sensor 122 are known, a technician may use the viscosity reading to confirm the hematocrit reading.

Another parameter that may be tested with magneto-elastic-resonance sensors is the actual glucose reading. For this purpose, sensors may be coated with glucose sensitive coatings, such as glucose binding protein, glucose oxidase, or any other suitable substrate for glucose. Again, these coatings swell when in the presence of glucose, altering the sensor's vibration characteristics. Although the glucose level can be tested for directly with typically acceptable results, one may use the hematocrit or viscosity level to further refine the glucose reading.

Figure 2C:
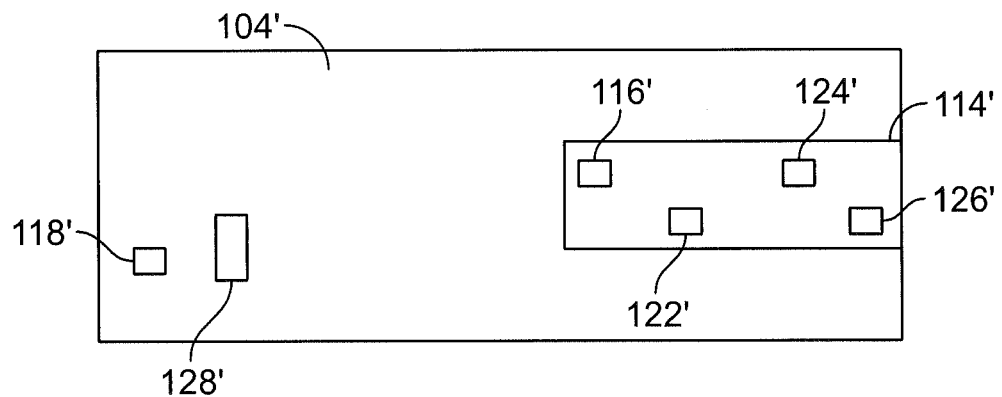

As can be seen from the foregoing, rather than providing only one or two particular types of tests, a test strip may be provided with multiple tests. Such a "total compensation" test strip, for example, may have sensors that are capable of interrogation for humidity, underfill, temperature, glucose, hematocrit (in the case of glucose strips), and viscosity. In this case, multiple sensors may be placed in and around the cavity, where each sensor represents a parameter or parameters to be tested for. For example, as shown in FIG. 2c, the test strip 104' can include a plurality of sensors, with some of the sensors 116', 122', 124', and 126' being positioned fully within the cavity 114', and other sensors 118', 128' being positioned outside of the cavity 114'. Each of the sensors 116', 122', 124', and 126' represents a parameter or parameters to be tested. In this example, test strip 104' may include one sensor 116' to measure underfill, the sensor being within the cavity 114'. A second sensor may detect temperature, although it is preferred that sensor 116' also do so. Meanwhile, a third sensor 122' may sense hematocrit levels while a fourth sensor 124' tests for humidity and a fifth sensor 126' tests for glucose (it is noted that no viscosity sensor is shown in this example, but one may be). Each of the sensors may operate individually as previously discussed in order to be interrogated. Such interrogation may be simultaneous or in series.

Figure 2D:
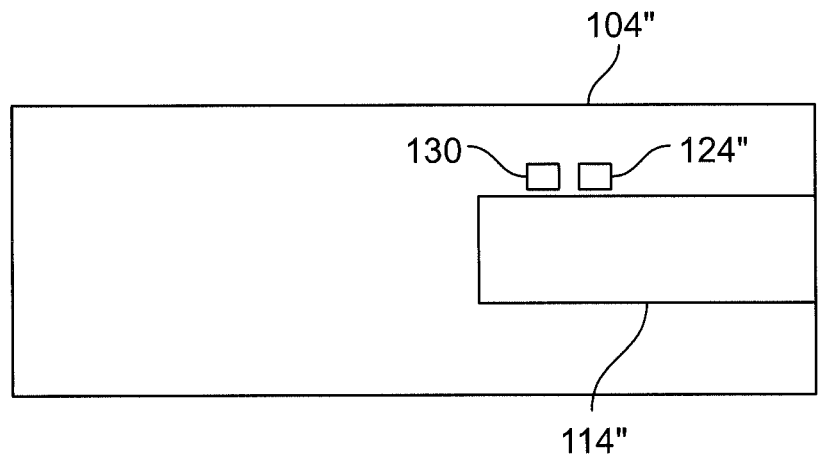

In preferred embodiments of the invention, a temperature sensor 130 and a humidity sensor 124" (FIG. 2d) may both be placed directly adjacent to the sample cavity 114" of a test strip. Given this placement in direct proximity of the cavity 114", accurate ambient humidity and temperature readings of the reaction within the cavity may be obtained. With these readings, the meter may use a calibration protocol to adjust the results of glucose or other testing.

Moreover, it is contemplated that a single sensor may be utilized to test for more than one condition. This has been discussed with reference to underfill and temperature, but that example was limited to one non-qualitative test and one qualitative test. It is also contemplated that multiple qualitative tests may be achieved using one sensor. In such a case, the sensor may be coated with multiple coatings, each of which being sensitive to the parameter being tested. Alternatively, the sensor may be coated with a single coating reactive to two parameters. Sophisticated deconvolution algorithms may then be used to extract the respective individual parameters from a single measurement.

In the test strip industry, a typical manufacturer will provide a test meter and a consumer will purchase the meter as a one time purchase. Test strips, on the other hand, are a commodity that are constantly used and replaced. There is therefore a great deal of value in preventing third parties from manufacturing test strips that can be used in another's meter. There is also a great deal of value in ensuring the public that the test strips being utilized are proper for the meter owned by the user.

Techniques for autocoding test strips are known. However, autocoding may also be achieved using the teachings of magneto-elastic-resonance sensors herein. For example, one or more sensors may be placed on the strip, the sensors having known lengths (governing the resonance characteristics) which may be consistent or varied within the strip. Meters may then have algorithms designed to interrogate the test strips to determine whether such magneto-elastic-resonance sensors are present, are in the correct locations, and have the correct resonance frequency when interrogated (usually by being of the correct length). Because of the extreme accuracy of magneto-elastic-resonance technology, it would be very difficult for one manufacturer to reverse engineer another's particular magneto-elastic-resonance sensor location and frequency characteristics. Yet, such would be easily repeatable for the original manufacturer that has knowledge of the given parameters. A sensor 128' of the type envisioned for autocoding of a test strip 104' is shown in FIG. 2c.

An example of magneto-elastic-resonance sensor technology is now provided. Example 1—Underfill detection In this example, an uncoated magneto-elastic-resonance sensor was utilized. The magneto-elastic-resonance sensor measured 2.5 mm×0.5 mm×30 µm and was cut from an etched sheet of Metglas 2826MB. A plastic measurement cavity was built up from two separate plastic sheets that were fused together with a heat gun. The magneto-elastic-resonance sensor was placed in the cavity of the test strip.

Figure 4:
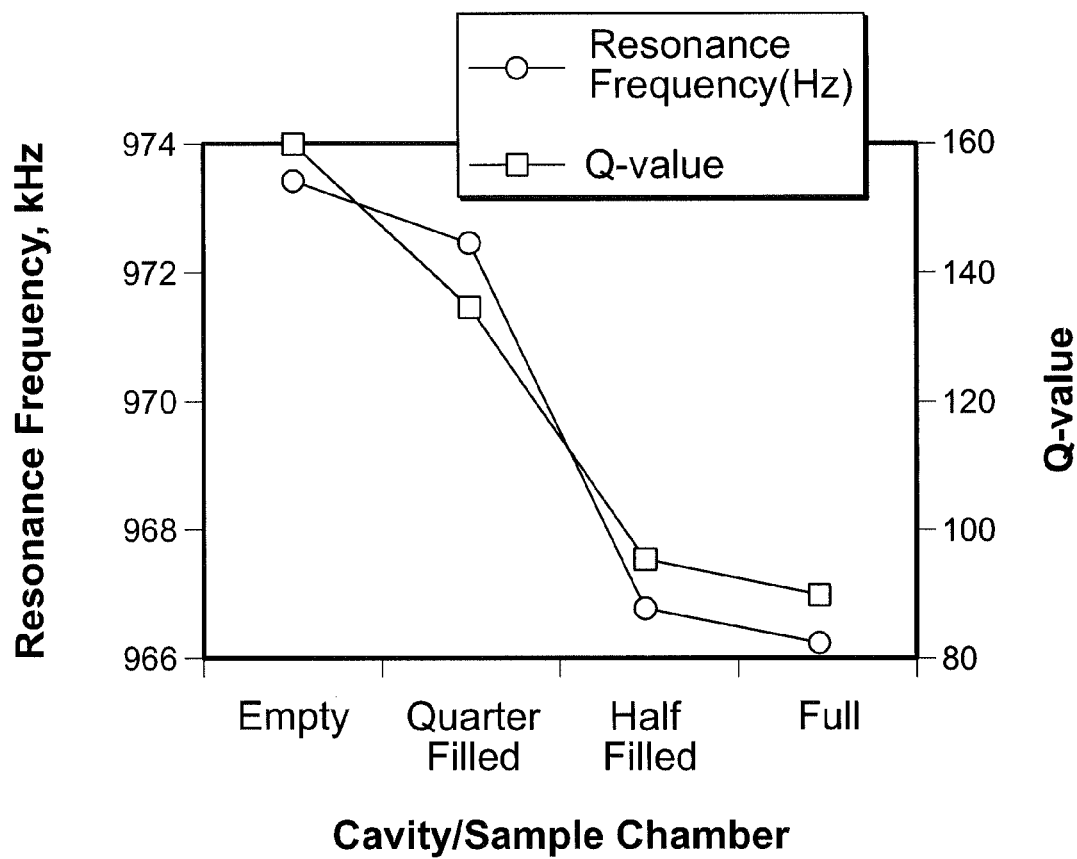
FIG. 4 depicts the graphical results of an example of underfill detection using magneto-elastic-resonance technology.

The magneto-elastic-resonance sensor was first interrogated with an empty cavity, then with quarter filled, half filled, and finally with a full cavity. The result is shown graphically in FIG. 4, with the frequency and Q-values being shown for each of the tests. From these tests it can be seen that it is difficult to distinguish between the half-full and full cavity. This is because capillary force pulls the liquid on top of the magneto-elastic-resonance sensor as soon as the liquid reaches the lower tip of the sensor. Note also that the Q-value dropped by 50%, however the change could be significantly higher if a humidity sensitive material was coated on the magneto-elastic-resonance sensor.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:

1. A test strip for testing a characteristic of a fluid sample applied to the test strip, the test strip comprising:
   a body of wicking material having a first surface and a second surface;
   a cavity within the wicking material; and
   at least one magneto-elastic-resonance sensor at least partially positioned within the cavity.

2. The test strip of claim 1, further comprising a second magneto-elastic-resonance sensor.

3. The test strip of claim 1, wherein the at least one magneto-elastic-resonance sensor is positioned closer to a top portion of the cavity than a bottom portion of the cavity.

4. The test strip of claim 3, wherein the at least one magneto-elastic-resonance sensor indicates whether a sufficient amount of the fluid sample is present in the cavity.

5. The test strip of claim 2, wherein the at least one magneto-elastic-resonance sensor and the second magneto-elastic-resonance sensor are coated with a characteristic sensitive coating.

6. The test strip of claim 5, wherein the characteristic sensitive coating is a temperature sensitive coating.

7. The test strip of claim 5, wherein the second magneto-elastic-resonance sensor is positioned adjacent the cavity, wherein the at least one magneto-elastic-resonance sensor is coated with a humidity sensitive coating and the second magneto-elastic-resonance sensor is coated with a different characteristic sensitive coating than the characteristic sensitive coating of the at least one magneto-elastic-resonance sensor.

8. The test strip of claim 7, further comprising a third magneto-elastic-resonance sensor, the cavity positioned between the second and third magneto-elastic-resonance sensors.

9. The test strip of claim 2, further comprising a third magneto-elastic-resonance sensor, the second and third magneto-elastic-resonance sensors positioned adjacent one another and away from the cavity.

10. The test strip of claim 1, further comprising a plurality of magneto-elastic-resonance sensors within the cavity.

11. The test strip of claim 1, wherein the wicking material comprises a cellulose material.

12. The test strip of claim 1, further comprising a lid overlying the cavity, the lid comprised of a liquid impervious protective material.

13. The test strip of claim 2, wherein the body includes a first end and a second end, the cavity positioned adjacent the first end, and the second magneto-elastic-resonance sensor positioned adjacent the second end.

14. The test strip of claim 2, wherein the at least one magneto-elastic-resonance sensor is located in a flow path of the fluid sample before the second magneto-elastic-resonance sensor, the second magneto-elastic-resonance sensor positioned adjacent the cavity.

15. The test strip of claim 1, wherein the at least one magneto-elastic-resonance sensor is coated with glucose oxidase.

16. The test strip of claim 1, wherein a portion of the at least one magneto-elastic-resonance sensor is partially positioned outside the cavity.

17. A test strip for testing a characteristic of a fluid sample applied to the test strip, the test strip comprising:
   a body of wicking material having a first surface and a second surface;
   a cavity within the wicking material, the cavity extending at least partially between the first and second surfaces of the body;
   at least one first magneto-elastic-resonance sensor positioned within the cavity; and at least one second magneto-elastic-resonance sensor positioned outside of the cavity.

18. A method of interrogating a test strip to identify a characteristic of a fluid sample, the method comprising:
applying a fluid sample to a test strip;
permitting the fluid sample to flow into a cavity within a wicking layer of the test strip so as to wet a magneto-elastic-resonance sensor positioned at least partially within the cavity;
transmitting an electromagnetic field into the test strip so as to excite the magneto-elastic resonance sensor;
obtaining a resultant oscillation frequency of the sensor; and
identifying a characteristic of the fluid sample based on the resultant oscillation frequency.

19. The method of claim 18, further comprising transmitting the signal in short pulses.

20. The method of claim 18, wherein the resultant oscillation frequency is a first resultant oscillation frequency, and wherein the step of transmitting further comprises transmitting the signal so that a second magneto-elastic-resonance sensor provided on or within the test strip is excited,
the method further comprising obtaining a second resultant oscillation frequency from the second magneto-elastic-resonance sensor; and comparing the second resultant oscillation frequency to the first resultant oscillation frequency, the step of identifying further comprising identifying the characteristic of the fluid sample based on the comparison between the first and second resultant oscillation frequencies.

* * * * *